United States Patent [19]
Aoe et al.

[11] Patent Number: 5,858,444
[45] Date of Patent: Jan. 12, 1999

[54] FOOD AND BEVERAGES HAVING DECREASED DIGESTIVE AND ABSORPTIVE PROPERTIES AND METHOD OF PREPARING THE SAME

[75] Inventors: Seiichirou Aoe, Sayama; Hiroaki Matsuyama, Kawagoe; Sachiko Yahagi, Iwatsuki; Masatoshi Yahiro, Higashimurayama; Hiroaki Konishi, Kawagoe; Tatsuji Kameoka, Kodaira; Kiyoshi Tatsumi, Iruma, all of Japan

[73] Assignee: Snow Brand Milk Products Co., Ltd., Hokkaido, Japan

[21] Appl. No.: 556,902

[22] PCT Filed: Mar. 31, 1995

[86] PCT No.: PCT/JP95/00619

§ 371 Date: Nov. 29, 1995

§ 102(e) Date: Nov. 29, 1995

[30] Foreign Application Priority Data

Mar. 31, 1994 [JP] Japan .................. 6-087385

[51] Int. Cl.$^6$ .................. A23L 1/308
[52] U.S. Cl. .................. 426/601; 426/519; 426/590; 426/611; 426/804
[58] Field of Search .................. 426/601, 611, 426/519, 804, 590

[56] References Cited

U.S. PATENT DOCUMENTS 4,849,242  7/1989  Kershner .................. 426/601
5,314,707  5/1994  Kester et al. .................. 426/611
5,431,949  7/1995  Meyer et al. .................. 426/611

OTHER PUBLICATIONS

Biosci. Biotech. Biochemistry, vol. 56, No. 6, pp. 1093–1096, 1994; "The Digestibility of Branched–chain Triacylglycerols and Their Effects on Plasma and Hepatic Lipid Levels in the Rat"; T. Tagiri, et al.

Journal of Agricultural and Food Chemistry, vol. 42, No. 2, 1994; "Review of Triacylglycerol Disgestion, Absorption, and Metabolism with Respect To SALATRIM Triacylglycerols"; J. R. Hayes, et al.; pp. 474–483.

American Journal of Clinical Nutrition, vol. 31, pp. 273–276, Oct. 1978; "Studies In Man Of Partially Absorbed Dietary Fats"; S. Hashim et al.

*Primary Examiner*—Helen Pratt
*Attorney, Agent, or Firm*—Townsend & Banta

[57] ABSTRACT

Foods and beverages having decreased digestive and absorptive properties characterized in containing 40 weight % or more all saturated acyl chain triglyceride consisting only of stearic acid and/or palmitic acid as an oil component. The all saturated acyl chain triglyceride consisting only or stearic acid and/or palmitic acid contained in the foods and beverages is not digested and absorbed in the bodies, so that calories may be decreased substantially.

4 Claims, No Drawings

FOOD AND BEVERAGES HAVING DECREASED DIGESTIVE AND ABSORPTIVE PROPERTIES AND METHOD OF PREPARING THE SAME

TECHNICAL FIELD

The present invention relates to foods and beverages the digestive and absorptive properties of which are decreased by blending a certain amount of all saturated acyl chain triglyceride consisting only of stearic acid and/or palmitic acid. The present invention relates also to a method of preparing the foods and beverages having decreased digestive and absorptive properties comprising blending an oil component containing all saturated acyl chain triglyceride consisting only of stearic acid and/or palmitic acid.

BACKGROUND ART

In recent years, the increase of patients suffered from geriatric diseases with the increase of the intake of oil has been given attention, and it has become considered that there is a strong relation between the oil intake and the crisis rates of arterial sclerosis, mammary cancer and colon cancer. Thus, the trend that the oil intake is kept at a distance is extended, and the oil substitutes utilizing polysaccharide and proteins are researched actively under present conditions. However, the popularity of oil is high so that it is very difficult to substantially decrease the oil intake in one's food life under the present circumstances. Further, the foods intended to essentially control the oil intake oils with paying attention to the digestive and absorptive properties of oils, have not developed yet.

It has been known that the digestive and absorptive properties of fats depend greatly on physical and chemical characteristics thereof, i.e., such as melting point and constituent fatty acid species. For example, the higher the melting point of an oil, the lower the digestibility and absorbability become, and the longer the carbon length of a saturated fatty acid, the lower the digestibility and absorbability become. Further, it has been known that the digestive and absorptive properties vary with the differences of the position and the combination of the fatty acids bonded to glycerol. For example, it has been reported that palmitic acid being saturated fatty acid, accelerates the absorptions of free fatty acids, in particular saturated fatty acids, since not only triglyceride bonded to 2-position is more excellent in digestive and absorptive properties than a triglyceride bonded to 1,3-position, but 2-palmitic monoglyceride produced in the process of digestion is excellent in emulsifying characters. On the other hand, it has been known that as the digestive and absorptive properties of stearic acid, the digestive and absorptive properties vary with the fatty acid constituting triglyceride. It has been reported, as the results of experiments using rats, that for example chemically synthesized tristearin is hardly digested or absorbed, but if one more two of the stearic acids within it are replaced by monounsaturated fatty acids, the stearic acid is almost absorbed. Further, it has been known that although triglycerides consisting of stearic acid and palmitic acid have very low digestive and absorptive properties, the digestive and absorptive properties are increased when it is ingested with the same amount of another liquid oil (Hashim et al., Am.J.Clin.Nutr., 31:S273–276, 1978). Therefore, it was unknown whether the digestive and absorptive properties may be decreased or not when the triglyceride consisting of stearic acid and palmitic acid is mixed with another oil and ingested.

The present inventors, in view of the above problems, have investigated repeatedly with paying attention to an all saturated acyl chain triglyceride consisting only of stearic acid and/or palmitic acid, and found that these triglycerides are hardly digested or absorbed. Further, the present inventors found that, even if an oil component containing these triglyceride is emulsified and added to foods and beverages or it is mixed with another oil components and emulsified and added to foods and beverages, yet the original oil mouth feel is kept, these triglyceride are hardly digested or absorbed. Thus the inventors completed the present invention. Therefore, an object of the present invention is to provide foods and beverages having digestive and absorptive properties which are decreased by blending a certain amount of all saturated acyl chain triglyceride consisting only of stearic acid and/or palmitic acid as an oil component. As a raw material for foods containing all saturated acyl chain triglyceride consisting only of stearic acid and/or palmitic acid, hardened oil is exemplified. As the past examples of the usages of the hardened oil in foods, the usage of the oil as a physical properties modifier for mayonnaise having low-temperature resistance (Japanese Examined Patent Publication No.62-25340), the usage of the oil as a physical properties modifier for liquid shortening (Japanese Examined Patent Publication No.Hei 3-12853), the usage of the oil in frozen tempura (Japanese Examine Patent Publication No.63-60977), the usage of the oil for low-temperature resistant edible oil and the like have been known. However, the usage of the hardened oil in foods and beverages which are intended to decrease the digestive and absorptive properties. As examples of the usages of the hardened oils as low-calorie oils. W/O emulsion for cooking (Japanese Un-Examined Patent Publication No.Hei 1-187052) has been known. However, in the publication, the physical properties are improved and the oil content of the emulsion may be decreased by adding the hardened oil, and as the results, the oil intake is decreased to attain the low-calorie. In addition, as low-calorie oils, the low-calorie oil (Japanese Un-Examined Patent Publication No.Hei 1-252248) and the oil for animal feeds (Japanese Un-Examined Patent Publication No.Hei 1-85040) and the like have been known, but all of them are concerned in the usage of triglyceride consisting of saturated fatty acid having 20 or more carbon atoms, and do not decrease the digestive and absorptive properties utilizing the character of the all saturated acyl chain triglyceride consisting only of stearic acid and/or palmitic acid.

DISCLOSURE OF INVENTION

In the present invention, the foods and beverages are prepared so as to contain 40 weight % or more all saturated acyl chain triglyceride consisting only of stearic acid and/or palmitic acid as an oil component. When the foods and beverages of the present invention are prepared, a variety of components constituting the foods and beverages may be mixed mechanically. As the oil component, an oil component containing 40 weight % or more all saturated acyl chain triglyceride consisting only of stearic acid and/or palmitic acid may be used as it is, or a mixed oil which was prepared by mixing with another oil so as to contain 40 weight % or more all saturated acyl chain triglyceride consisting only of stearic acid and/or palmitic acid may be used. In addition, as the oil component, it is more preferable that it is emulsified previously and added to foods and beverages. The reasons is that problems may appear, such as the difficulties of dispersing and mixing occurred when a high melting point oil is used mainly and when oil is mixed with raw materials constituting water phase of foods using oil; thermal denature and browning of the another components due to the mixing in a heating and melting state; and the difficulties of the washing of contamination due to the attachment of the high melting point oil to a manufacturing devices. Therefore, by emulsifying previously and adding to foods and beverages, these problems may be solved.

The foods and beverages thus obtained by the present invention functions sufficiently as a low-calorie oil containing foods and beverages and have unique mouth feel of oils. As the oil containing 40 weight % or more the all saturated acyl chain triglyceride consisting only of stearic acid and/or palmitic acid which may be used in the present invention, fully hydrogenated oils of e.g. corn oil, soybean oil, rapeseed oil, sun flower oil, safflower oil, high-oleic safflower oil, olive oil may be exemplified. The oil which may be used by mixing the all saturated acyl chain triglyceride consisting only of stearic acid and/or palmitic acid, is preferably liquid oil from the mouth feel, but even if any oil ia used, it does not effect on the absorptive characteristics of the all saturated acyl chain triglyceride consisting only of stearic acid and/or palmitic acid.

As the oil containing 40 weight % or more all saturated acyl chain triglyceride consisting only of stearic acid and/or palmitic acid, the oil which was heated and melted to the melting point or more may be used, and the oil which was emulsified previously using emulsifier such as monoglyceride, sorbitan fatty acid ester and stabilizer such as sodium caseinate. The size of the fat globules of the emulsified materials may be adjusted depending on the conditions of homogenizing pressure, homogenizing times, temperature, homogenizing valve shape and the like.

EXAMPLES

The present invention will be explained concretely by way of Examples hereinafter.

Example 1

Canola oil was fully hydrogenated according to a conventional method, and hardened canola oil was prepared. That is, after fully hydrogenating the canola oil under hydrogen atmosphere with nickel catalyst at 200° C. for one hour, the nickel catalyst was removed, and the oil was bleached to obtain the hardened canola oil. The constituent fatty acids of the hardened canola oil were 90.2 weight % stearic acid and 6.8 weight % palmitic acid. The content of the all saturated acyl chain triglyceride consisting only of stearic acid and/or palmitic acid was 95 weight %.

Then, cream containing the hardened canola oil was prepared in the ratio shown in Table 1. As for the raw materials, after dissolving and mixing them at 85° C. previously, these materials were emulsified at a homogenizing pressure of 500 kg/cm², and sterilized under conditions of 140° C. and 5 seconds.

TABLE 1

|  | (weight %) |
| --- | --- |
| Hardened Canola Oil | 25.00 |
| Skim Milk Powder | 3.25 |
| Sodium Caseinate | 2.80 |
| Water | 67.95 |
| Emulsifier | 1.00 |

To the cream thus prepared, skim milk (fat content is 0.8 weight %) was added so as to have a fat content of 3.5 weight %, and a milk beverage was prepared. Then an organoleptic evaluation was carried out by 20 panels on the mouth feel of the milk beverage. As a control milk beverages a low-fat milk having a fat content of 0.8 weight % was used. The results will be shown in Table 2.

TABLE 2

|  | Control | The Present Invention |
| --- | --- | --- |
| Intensity | None (20/20) | Yes (18/20) |
| Fat Feel | None (20/20) | Yes (16/20) |
| Milk Flavor | a little yes (12/20) | Yes (18/20) |

(Numbers of Answers/Number of Panels)

As shown clearly in the above results, the milk beverage of the present invention improved the mouth feel of the low-fat milk, and made mouth feel similar to bovine milk, in spite of having almost the same substantial calorie as the low-fat milk.

Example 2

Corn oil was fully hydrogenated according to a conventional method, and hardened corn oil was prepared. That is, after fully hydrogenating the corn oil under hydrogen atmosphere with nickel catalyst at 200° C. for one hour, the nickel catalyst was removed, the oil was bleached, and the hardened corn oil was obtained. The constituent fatty acids of the hardened corn oil were 88.0 weight % stearic acid and 11.1 weight % palmitic acid. The content of the all saturated acyl chain triglyceride consisting only of stearic acid and/or palmitic acid was 98 weight %.

Then, cream containing 50 weight % the hardened corn oil and 50 weight % canola oil was prepared in the ratio shown in Table 3. As for the raw materials, after dissolving and mixing them at 85° C. previously, these were emulsified at a homogenizing pressure of 500 kg/cm² and sterilized under conditions of 140° C. and 5 seconds.

TABLE 3

|  | (weight %) |
| --- | --- |
| Hardened Corn Oil | 12.50 |
| Canola Oil | 12.50 |
| Skim Milk Powder | 3.25 |
| Sodium Caseinate | 2.80 |
| Water | 67.95 |
| Emulsifier | 1.00 |

The cream thus prepared had the same mouth feel as the cream prepared using vegetable fats, and were not separated even if added to coffee drink, and had good flavor.

Example 3

Low-calorie cookies were prepared using the hardened rapeseed oil containing 95% all saturated acyl chain triglyceride (78% tristearin, 16% distearyl palmitin, 1% dipalmitoyl stearin). 90 parts sugar was added to 30 parts lightly whipped butter, and these were creamed. Meringue prepared by whipping 30 parts egg white and a small amount of vanilla flavor were added to it, and stirred to make cream. A mixture obtained by adding 30 parts the hardened rapeseed oil fine powders having an average particle size of 20 μm to 100 parts sieved soft flour, was mixed in the cream lightly to make cookie dough. A baking sheet was spread over a tin-pan, and the cookie dough was cut into a rubber mold having 25 rectangular holes having a size of 35 mm in length, 50 mm in width and 2 mm in height, and shaped and baked in a pre-heated oven at 200° C. for 5 to 7 minutes, to prepare langue-de-chat type cookies having good texture and good taste and flavor.

Test Example 1

An animal experiment using rats will be illustrated on the absorptive properties of the cream prepared in Example 1. A cream containing 25 weight % canola oil prepared using the same components as described in Example 1, was used as a control. The SD strain, male rats having body weights of 400 g were used, and they were divided into two groups, each group consisting of 4 animals. As the rats, laparotomy was carried out under etherization, and a polyethylene tube (0.75 mm, SP50, manufactured by Natsume Seisakusho KK) was cannulated the mesentery lymphoduct, and at the same time a polyethylene tube (0.50 mm, SP40, manufactured by Natsume Seisakusho KK) was inserted into the upper part of the stomach. After the operation, the abdominal parts were sutured, and the rats were fixed to Bollman cage, then physiological saline containing 5 weight % dextrose was fed at a rate of 3.0 ml/hr for one night with a peristaltic pump. After that, making sure that the flow rate of the lymph was stabilized, the test cream was diluted with water so as to have a fat concentration of 10 weight %, and the oil delivered into the mesentery lymphoduct was measured. The test cream was injected with a peristaltic pump at a rate of 3.5 ml/hr for 30 minutes. Then the lymph was collected with a fraction collector every one hour, and the triglyceride amount in the lymphoduct was determined by an enzyme method (Determiner TGS555), and the absorbability was calculated. In Table 4, the absorbabilities of the test cream on the 3rd hours and 6th hours after injection will be shown.

TABLE 4

|  | the 3rd hour (%) | the 6th hour (%) |
| --- | --- | --- |
| Canola Oil Cream | 53.3 ± 16.2 | 81.6 ± 7.2 |
| Hardened Canola Oil Cream | 4.0 ± 1.5* | 7.4 ± 1.0* |

*Significant difference from the control canola cream (p < 0.01) was found.

As clearly shown in the above results, the absorbabilities of the hardened canola oil cream were 1/10 or less of those of the canola oil cream.

Test Example 2

An animal experiment using rats will be illustrated on the absorptive properties of the cream prepared in Example 2. A cream containing 100 weight % corn oil prepared using the same components as described in Example 2, was used as a control. The SD strain, male rats having body weights of 400 g were used, and they were divided into two groups, each group consisting of 4 animals. As the rats, laparotomy was carried out under etherization, and a polyethylene tube (0.75 mm, SP50, manufactured by Natsume Seisakusho KK) was cannulated the mesentery lymphoduct, and at the same time a polyethylene tube (0.50 mm, SP40, manufactured by Natsume Seisakusho KK) was inserted into the upper part of the stomach. After the operation, the abdominal parts were sutured, and the rats were fixed to Bollman cage, then physiological saline containing 5 weight % dextrose was fed at a rate of 3.0 ml/hr for one night with a peristaltic pump. After that, making sure that the flow rate of the lymph was stabilized, the test cream was diluted with water so as to have a fat concentration of 10 weight %, and the oil delivered into the mesentery lymphoduct was measured. The test cream was injected with a peristaltic pump at a rate of 3.5 ml/hr for 30 minutes. Then the lymph was collected with a fraction collector every one hour, and the triglyceride amount in the lymphoduct was determined by an enzyme method (Determiner TGS555), and the absorbability was calculated. In Table 5, the absorbabilities of the test cream on the 3rd hours and 6th hours after injection will be shown.

TABLE 5

|  | the 3rd hour (%) | the 6th hour (%) |
| --- | --- | --- |
| Corn Oil Cream | 50.5 ± 10.1 | 85.7 ± 9.2 |
| Hardened Corn Oil Cream | 16.1 ± 10.2* | 36.5 ± 15.6* |

*Significant difference from the corn oil cream (p < 0.01) was found.

As clearly shown in the above results, the absorbability of the hardened corn oil cream were ½ or less of those of the corn oil cream. That is, it was shown that the calorie of oil was decreased to half or less, by blending 50 weight % the hardened corn oil.

Industrial Applicability

Since the all saturated acyl chain triglyceride consisting only of stearic acid and/or palmitic acid is not digested and absorbed in the bodies, foods and beverages having substantially decreased calories may be provided by blending a certain amount of all saturated acyl chain triglyceride consisting only of stearic acid and/or palmitic acid in the foods and beverages.

We claim:

1. A method of preparing foods and beverages having decreased digestive and absorptive properties comprising the step of blending a fully hydrogenated oil which was adjusted so that the content of the all saturated acyl chain triglyceride consisting only of stearic acid and/or palmitic acid in it is 40 weight % or more with another oil.

2. A method of preparing foods and beverages having decreased digestive and absorptive properties as claimed in claim 1, wherein the fully hydrogenated oil is previously emulsified and mixed.

3. A method of preparing foods and beverages having decreased digestive and absorptive properties, comprising the step of blending a mixed oil of fully hydrogenated oil and another oil which was adjusted so that the content of the all saturated acyl chain triglyceride consisting only of stearic acid and/or palmitic acid in it is 40 weight % or more.

4. A method of preparing foods and beverages having decreased digestive and absorptive properties as claimed in claim 3, wherein the mixed oil of fully hydrogenated oil and another oil is previously emulsified and mixed.

* * * * *